United States Patent
Taherian et al.

(10) Patent No.: US 8,471,559 B2
(45) Date of Patent: Jun. 25, 2013

(54) DOWNHOLE MICRO MAGNETIC RESONANCE ANALYZER

(75) Inventors: Reza Taherian, Sugar Land, TX (US); Krishnamurthy Ganesan, Sugar Land, TX (US); Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 553 days.

(21) Appl. No.: 12/299,322

(22) PCT Filed: May 2, 2007

(86) PCT No.: PCT/US2007/010737
§ 371 (c)(1), (2), (4) Date: May 21, 2009

(87) PCT Pub. No.: WO2007/130516
PCT Pub. Date: Nov. 15, 2007

(65) Prior Publication Data
US 2009/0219019 A1  Sep. 3, 2009

Related U.S. Application Data

(60) Provisional application No. 60/746,303, filed on May 3, 2006.

(51) Int. Cl.
*G01V 3/00* (2006.01)
*G01R 33/20* (2006.01)

(52) U.S. Cl.
USPC ........... 324/303; 324/321; 324/318; 324/306; 324/307; 324/309

(58) Field of Classification Search
USPC .... 324/300–322; 600/407–435; 382/128–131
See application file for complete search history.

(56) References Cited

U.S. PATENT DOCUMENTS

| | | | |
|---|---|---|---|
| 3,087,840 A * | 4/1963 | Shaw | 366/108 |
| 5,585,723 A | 12/1996 | Withers | |
| 5,950,543 A * | 9/1999 | Oster | 104/138.1 |
| 6,194,900 B1 | 2/2001 | Freeman et al. | |
| 6,346,813 B1 | 2/2002 | Kleinberg | |
| 7,141,978 B2 | 11/2006 | Peck et al. | |

(Continued)

FOREIGN PATENT DOCUMENTS

| | | |
|---|---|---|
| CN | 1707290 A | 12/2005 |
| WO | WO02056049 | 7/2002 |
| WO | WO2005/073695 | 8/2005 |

OTHER PUBLICATIONS

Van Bentum, P. et al., Towards Nuclear Magnetic Resonance (MU)-Spectroscopy and (MU)-Imaging, Analyst, Royal Society of Chemistry, London, GB, vol. 129, No. 9, 2004, pp. 793-803.

Wensink, H. et al., High Signal to Noise Ratio in Low Field NMR on Chip, Simulations and Experimental Results, Micro Electro Mechanical Systems, 2004, 17th IEEE International Conference on (MEMS), Maastricht, Netherlands, Jan. 25-29, 2004, pp. 407-410.

(Continued)

*Primary Examiner* — Melissa Koval
*Assistant Examiner* — Tiffany Fetzner
(74) *Attorney, Agent, or Firm* — John Vereb

(57) ABSTRACT

A downhole micro MR analyzer for use in a wellbore, having a micro sample tube, a micro RF coil in close proximity to the micro sample tube, and one or more magnets disposed about the micro sample tube is disclosed. The micro MR analyzer can be used for nuclear magnetic resonance or electron spin resonance experiments to ascertain formation properties and chemical compositions.

19 Claims, 4 Drawing Sheets

U.S. PATENT DOCUMENTS

| | | | |
|---|---|---|---|
| 7,596,402 B2 * | 9/2009 | Duerk et al. | 600/423 |
| 8,143,896 B2 * | 3/2012 | McDowell et al. | 324/322 |
| 2002/0140425 A1 | 10/2002 | Prammer et al. | |
| 2005/0054914 A1 * | 3/2005 | Duerk et al. | 600/423 |
| 2005/0253587 A1 * | 11/2005 | Peck et al. | 324/321 |
| 2005/0270023 A1 | 12/2005 | Freedman | |
| 2009/0146658 A1 * | 6/2009 | McDowell et al. | 324/309 |
| 2009/0219019 A1 * | 9/2009 | Taherian et al. | 324/303 |
| 2010/0264917 A1 * | 10/2010 | Budker et al. | 324/307 |
| 2012/0112744 A1 * | 5/2012 | McDowell et al. | 324/309 |
| 2012/0169334 A1 * | 7/2012 | Hopper et al. | 324/303 |

OTHER PUBLICATIONS

Massin, C. et al., Planar Microcoil-Based Microfluidic NMR Probes, Journal of Magnetic Resonance, Academic Press, Orlando, FL, US, vol. 164, No. 2, Oct. 2003, pp. 242-255.

International Preliminary Report on Patentability of PCT Application Serial No. PCT/US2007/010737 dated Nov. 4, 2008.

Second Office Action to Chinese Patent Application Serial No. 200780020503.3 dated Apr. 27, 2012.

* cited by examiner

DOWNHOLE MICRO MAGNETIC RESONANCE ANALYZER

CROSS-REFERENCE TO RELATED APPLICATIONS

This application claims priority to and the benefit of U.S. Provisional Application No. 60/746,303, filed May 3, 2006.

BACKGROUND

1. Field of Invention

The present invention pertains to downhole nuclear magnetic resonance (NMR) tools for use in a wellbore, particularly small-scale downhole NMR tools.

2. Related Art

Downhole NMR tools are commonly used, in oil and gas exploration, for example, to ascertain or infer properties of the subsurface formations encountered by a wellbore. Downhole NMR tools may be used while drilling the wellbore, or may be run into the wellbore after drilling, for example, on a wireline. Various reservoir fluid properties can be measured using a downhole NMR tool. Measurements can be made on reservoir fluids in the formation, or measurements can be made on a fluid sample withdrawn from the formation or wellbore. The NMR tool can be a stand-alone tool or may be incorporated as a module in a fluid sampling tool such as that disclosed in U.S. Pat. No. 6,346,813 B1 issued to Kleinberg. An example of a formation fluid tester tool is the Modular Formation Dynamics Testing tool marketed under the trade name of MDT™ by Schlumberger Technology Corp. (Houston, Tex.).

A downhole NMR tool generally includes a magnet that produces a static magnetic field over the volume of the fluid sample. The NMR tool also includes a coil or antenna to produce radio frequency (RF) pulses. The magnetic dipole moment of the RF antenna is substantially perpendicular to the magnetic dipole moment of the static magnetic field. In addition, the NMR tool may include one or more gradient coils.

The static field of a downhole NMR tool is generally too inhomogeneous to allow NMR spectroscopy to be performed. The inhomogenieties are attributed to variations in the magnetic material comprising the magnets and the magnet configuration. Thus, the static magnetic field inhomogenieties over the sample volume are to too large to perform NMR spectroscopy, but is generally acceptable for conventional NMR measurements such as relaxation times and diffusion.

SUMMARY

A downhole micro MR analyzer for use in a wellbore, having a micro sample tube, a micro RF coil in close proximity to the micro sample tube, and one or more magnets disposed about the micro sample tube is disclosed. The micro MR analyzer can be used for nuclear magnetic resonance or electron spin resonance experiments to ascertain formation properties and chemical compositions.

DETAILED DESCRIPTION

This invention relates to a lab-on-a-chip/micro magnetic resonance analyzer and method of using same. A micro magnetic resonance analyzer (micro MR analyzer) can measure nuclear spins or electron spins. One that measures nuclear spins is referred to as a micro NMR analyzer, and one that measures electron spins is referred to as a micro ESR analyzer. Although the discussion below is directed to a micro NMR analyzer, it is equally applicable to a micro ESR analyzer.

Figure 1:
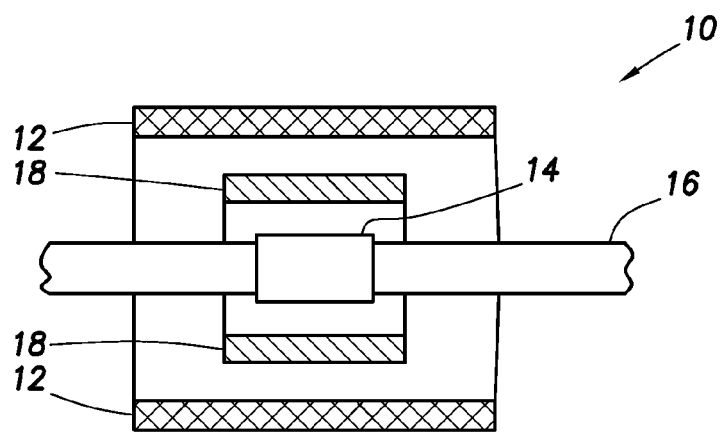
FIG. 1 shows one embodiment of a micro NMR analyzer constructed in accordance with the present invention.

As shown in FIG. 1, the micro NMR analyzer 10 has a micro or macro sized magnet 12, a micro RF coil 14, a micro sample tube 16, and optionally a micro gradient coil 18. The micro RF coil antenna 14 (coil diameter <1 mm) may be built using micro-fabrication techniques. Since the micro RF coil 14 (or probe) is small, the NMR sensitive region is also small and the static magnetic field inhomogeneity will be small over this region. As a result, it is possible to make NMR measurements using the micro NMR analyzer 10 even though the static magnetic field is non-homogeneous when considered over larger dimensions. Because the electrical power required to excite the NMR spins with the micro RF coil 14 is small, a miniaturized magnetic resonance spectrometer can be built. The gradient coils 18 can also be constructed using micro-fabrication techniques, including electroplating technology. Micro-fabrication techniques are effective in establishing accurate geometries and good mechanical stability for the tool components.

FIG. 1 shows a micro NMR analyzer 10 for downhole fluid analysis constructed on a small (micro) scale relative to existing NMR analysis devices. The micro NMR analyzer 10 is connected to supporting electronics (not shown) for excitation and data acquisition. The supporting electronics may be different for a micro ESR analyzer, but serves effectively the same purpose. The micro NMR analyzer 10 uses very small fluid sample volumes on which to make measurements to obtain various fluid properties like viscosity, spin-lattice relaxation time (T1), spin-spin relaxation time (T2), molecular diffusion (D), molecular composition, hydrogen index (HI), and water saturation ($S_w$). The micro NMR analyzer 10 can be used alone or in conjunction with the Schlumberger Modular Dynamics Tester (MDT) tool or a similar sampling tool.

Figure 2:
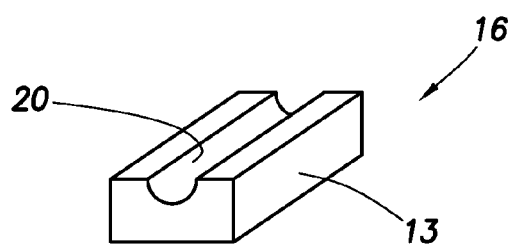
FIG. 2 shows one embodiment of a sample delivery half channel that may be used in the micro NMR analyzer of FIG. 1.

FIG. 2 shows in part one embodiment of the sample tube 16. In this embodiment, sample tube 16 comprises two pieces of non-conductive material such as glass, ceramic, or a polymer. FIG. 2 shows one of the two pieces. The two pieces have channels 20 cut into them, for example, by etching techniques. When the two pieces are brought together, the two channels 20 align to form a passageway with a desired cross-sectional shape. The cross-sectional dimensions of the sample tube 16 help determine the flow rate and is a design parameter available to the system designer. Because micro-fabrication techniques are used, the path and cross-sectional area of the sample tube 16 can be well-controlled and allows for complicated design choices. More than two pieces can be used to form the sample tube 16. Alternatively, a capillary tube can be used as a sample tube 16.

Figure 3:
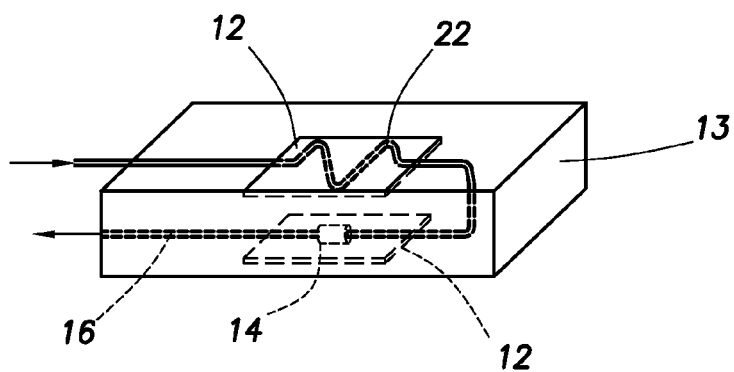
FIG. 3 shows one embodiment by which the pre-polarization length that may be used in the micro NMR analyzer of FIG. 1.

To pre-polarize the fluid before it enters the measurement volume, an elongated sample delivery channel 22 can be added to the sample tube 16. The sample delivery channel 22 can be a straight section of channel as described above, or is preferably a channel traversing a winding or helical path in the vicinity of the measurement volume, as shown in FIG. 3. The latter approach reduces the size of the magnet needed to create the pre-polarization. Depending upon the pre-polarizing path length, the NMR measurement can be done at a slow flow rate or in a mode in which the fluid is stopped (stopped mode).

In addition to generating $B_0$ for NMR measurement, a rather long section of DC (i.e., static) magnetic field is needed for pre-polarization. It is preferable to have as large a pre-polarizing magnetic field as possible. The homogeneity requirements, however, are not as stringent in the pre-polarization region as they are in the NMR measurement volume, as discussed further below.

The NMR signal-to-noise ratio is, among other factors, proportional to the 7/4 power of $B_0$. Thus it is desirable to use as large a $B_0$ field as possible in the micro NMR analyzer 10. A first parameter of interest in the magnet design is the strength of the magnet 12, which should be as strong as possible. This is achieved primarily by keeping the sample as close to the magnet 12 as possible. A second parameter is the homogeneity of the magnetic field. The field should be made as homogeneous as possible. While a larger magnetic field is desired, one must always be aware that space limitations and other geometric constraints, as well as temperature considerations, can limit magnet selection.

The magnetic field can be generated by a direct current circulating in a coil, or by using a permanent magnetic material such as samarium cobalt (SmCo). For a given magnet size, the magnetic field strength of a superconducting electromagnet is larger than that of a permanent magnet, which in turn is larger than the magnetic field of an electromagnet made with non-superconducting wires. All three types of magnet designs are feasible and within the scope of the present invention. The choice depends on various factors such as the complexity of the instrumentation and the expense. For example, a superconducting magnet can generate the largest and most homogeneous magnetic field, but requires cryogenics and maintenance, while a permanent magnet is carefree, but variations in material may lead to somewhat inhomogeneous fields that for some applications would compromise the tool's performance.

Preferred embodiments use permanent magnets 12. Using the micro-fabrication approach, the magnets 12 can be deposited directly on the "chip" or substrate material 13 comprising the sample tube 16. Using the macro approach, a permanent magnet 12 can be made easily. Two parallel magnets can form a reasonably homogeneous magnetic field, as is known in the art. The field produced by the permanent magnets 12 has variations caused by variations in the magnetic material. Those variations in the field are proportional to the size of the smaller blocks used to construct the magnet 12. However, the NMR measurement volume, which is proportional to the sample size, is very small and can be made to be much smaller than the relevant block size. Thus it is possible to perform NMR measurements in a substantially homogeneous region. Since the sample tube 16 and the micro RF coils 14 can be made very small, the two permanent magnets 12 can be brought very close to each other, thereby increasing the magnetic field permeating the sample volume. The small size of the NMR sensitive volume helps with the $B_0$ homogeneity requirement, thus allowing the use of virtually any method of generating a static magnetic field. In another embodiment, more than two magnets 12 can be used to produce $B_0$. It is well known in the art that arranging six or more magnets in a particular field orientation can form a cylindrically shaped homogeneous magnetic field that is very well suited for this application.

Figure 4:
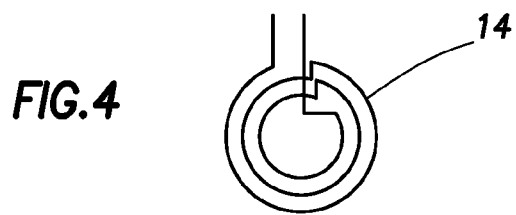
FIG. 4 shows one embodiment of a spiral coil that may be used in the micro NMR analyzer of FIG. 1.
Figure 5:
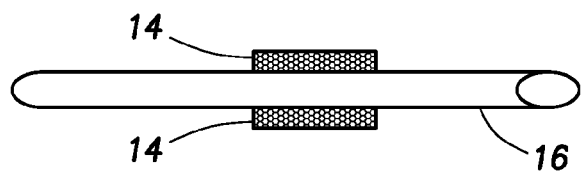
FIG. 5 shows one embodiment of a Helmholtz coil that may be used in the micro NMR analyzer of FIG. 1.

Various embodiments of micro RF coils 14 may be used in the present invention. While preferred frequencies are in the RF range, the invention is not limited to those frequencies. The planar nature of some of these coils is ideal in space-constrained locations. In one embodiment, the invention comprises a Helmholtz coil, that is, having two coils arranged with their planes parallel and separated a distance equal to the diameter of the coils. This coil arrangement produces a very homogeneous magnetic field in the space between the two coils and is ideal for the current application. For space reduction and ease of construction by micro-fabrication techniques, the two coils 14 can be made of spiral shape as shown in FIG. 4. The spiral portion of the coil 14 can be etched on a printed circuit board and attached to the sample tube 16, but a preferred embodiment is to etch the coils 14 directly onto the sample tube 16. The thickness and width of the conductive material (e.g., copper) comprising the spiral portion can be small (e.g., <1 mm). The two coils 14 may be placed on opposite sides of the sample tube 16, as shown schematically in FIG. 5. The coil diameter/separation distance should be chosen so as to produce a homogeneous field throughout the sample volume, and preferably in the closest possible proximity to the sample tube 16.

Figure 6:
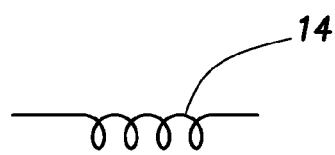
FIG. 6 shows one embodiment of a solenoid coil that may be used in the micro NMR analyzer of FIG. 1.

A solenoid-shaped micro coil 14 is shown in FIG. 6 and may be used in the present invention. Similar to the Helmholtz coil embodiment described above, the diameter of the solenoid RF coil 14 may be relatively small (e.g., <1 mm). The coil 14 may be wound around the sample tube 16, but preferably is micro-fabricated with the winding disposed directly on the sample tube 16. This allows more control on the field homogeneity and helps reduce acoustic ringing. This embodiment is particularly useful for a capillary tube used as a sample tube 16. Again, the coil 14 is preferably placed in the closest possible proximity to the sample volume. Such a configuration produces a substantially homogenous field within the sample volume and optimizes the "filling factor" (percentage of coil interior occupied by the sample) of the coil 14.

Figure 7:
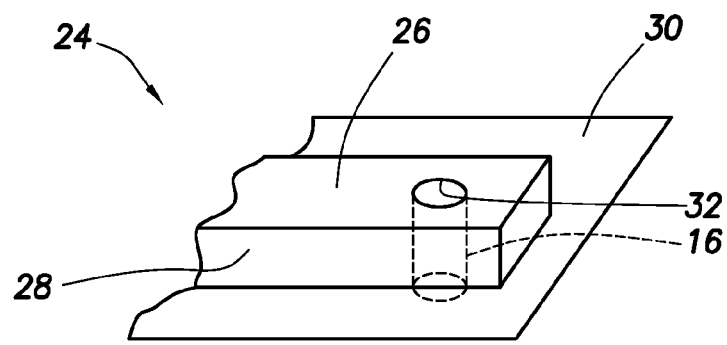
FIG. 7 shows one embodiment of a slitted micro strip that may be used in the micro NMR analyzer of FIG. 1.

A further embodiment of a micro RF coil 14 comprises a conventional micro-strip line 24 having a first conductive trace 26 on top of a dielectric material 28 mounted onto a ground plane 30 (a second conductive trace). The impedance is determined by the width of the first conductive trace 26, the dielectric constant of the dielectric material 28, and the separation distance between the two conductive traces 26, 30. The conventional micro strip line 24 can be machined or etched to form a small (e.g., <<one wavelength) slit 32 through the micro strip 24 (see FIG. 7). The passageway created by the slit 32 forms the sample tube 16. As before, this embodiment may be fabricated using micro-fabrication techniques.

Figure 8:
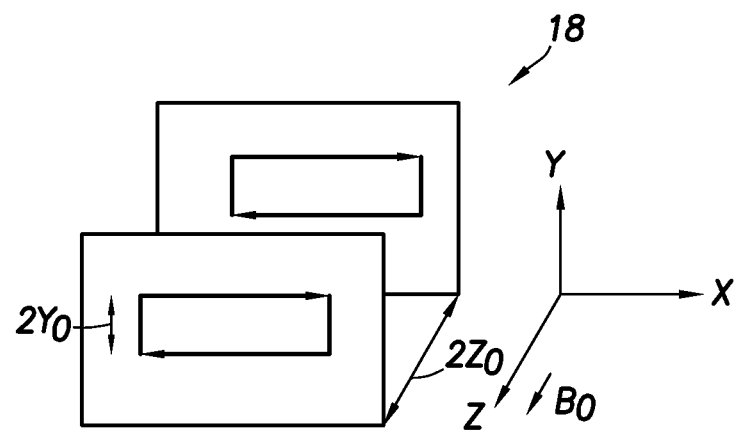
FIG. 8 shows a configuration that may be used in the micro NMR analyzer of FIG. 1 to produce a Z-axis (dBz/dZ) gradient coil.
Figure 9:
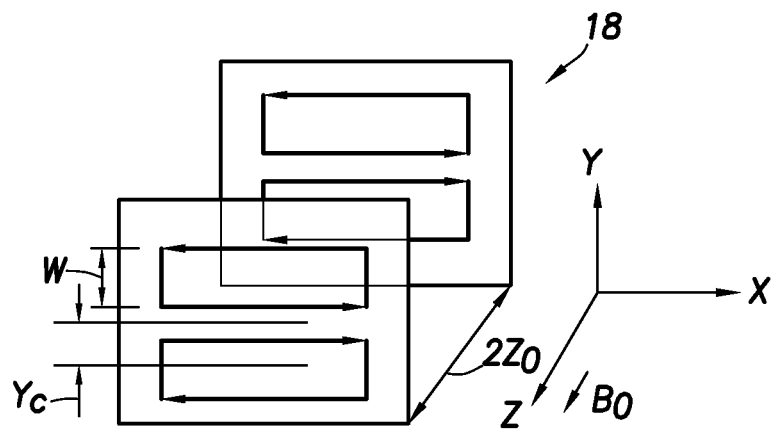
FIG. 9 shows a configuration that may be used in the micro NMR analyzer of FIG. 1 to produce a Y-axis (dBz/dY) gradient coil.
Figure 10:
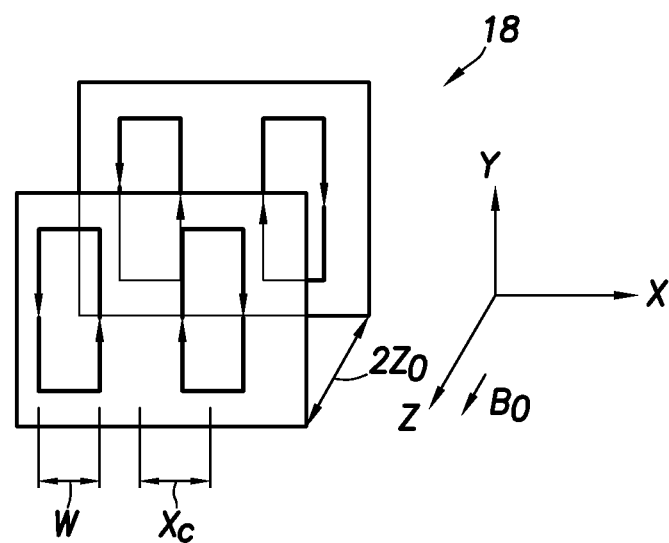
FIG. 10 shows a configuration that may be used in the micro NMR analyzer of FIG. 1 to produce an X-axis (dBz/dX) gradient coil.

Gradient coils 18 can be used to study diffusion and for imaging. Because of the planar nature of the gradient coils 18, they can also be constructed using micro-fabrication techniques, and therefore do not occupy too much space. Self-diffusion studies on fluid samples require a gradient in only one direction. Various coil arrangements producing various gradients are shown in FIGS. 8, 9, and 10. Other more sophisticated measurements such as imaging may require other, more complicated gradients. Combinations of the various coil arrangements described above may be used to provide the more complicated gradients.

Figure 11:
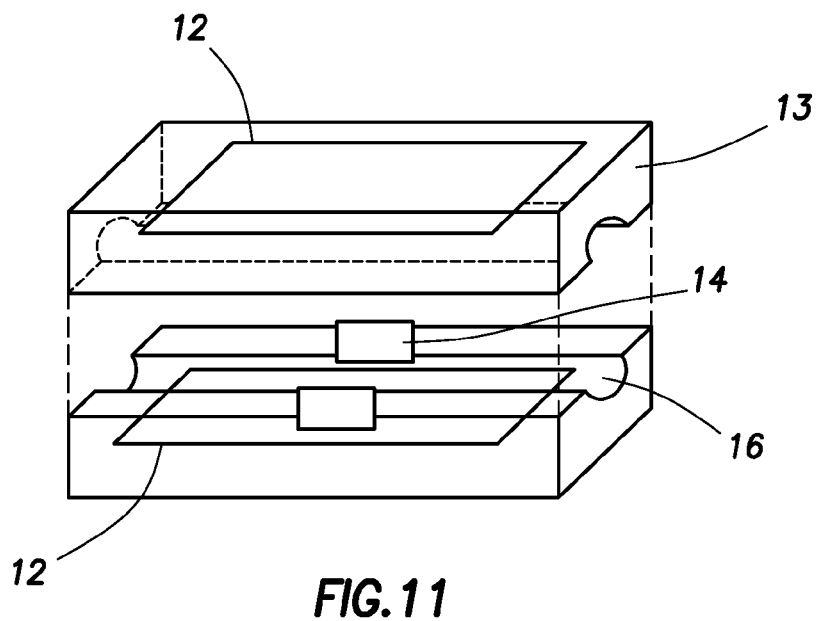
FIG. 11 shows an embodiment of the micro NMR analyzer of FIG. 1 using a permanent magnet.

The embodiment shown in FIG. 11 comprises two opposing permanent magnets 12 positioned on either side of the sample tube 16. The magnets 12 are either deposited on the faces of the chip or they can be macro permanent magnets placed near those surfaces. A permeable magnetic pole piece (see FIG. 12) can also be used to focus the field and thereby increase the homogeneity of the magnet. The magnetic field strength depends on the characteristics of the magnetic material and the dimensions of the magnet. This configuration may be used to perform NMR studies during flow and also at stopped mode. The magnet 12 is longer than the micro RF coil 14 to allow pre-polarization of the spins before detection. The micro RF coils 14 are micro-fabricated on the two faces of the chip that are normal to the magnets 12. Permeable magnetic materials that are operable in the RF range can also be used enhance the magnetic field of the micro RF coils 14. Permeable magnetic materials can also be used to enhance the performance of gradient coils 18.

Figure 12:
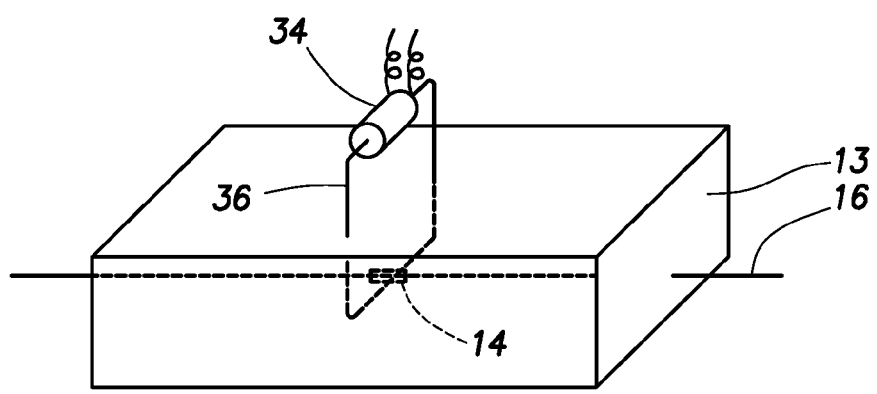
FIG. 12 shows an embodiment of the micro NMR analyzer of FIG. 1 using an electromagnet.

The embodiment shown in FIG. 12 uses electromagnets 34. A static $B_0$ field is focused on the sensing (measurement) volume using permeable magnetic rods 36 that form a C-type magnet. The design as shown performs the NMR measurement in stopped mode because there is no pre-polarization of spins for flowing spins. However, pre-polarization can be added. The $B_1$ field is provided by a micro RF coil 14 or, alternatively, Helmholtz-type coils can be fabricated on the side faces.

The two- and three-dimensional NMR techniques described above can be used to characterize reservoir fluid properties using NMR logging tools. Typical NMR molecular dynamic parameters such as T1, T2, and D can be measured with the present invention. In addition, the chemical shift or NMR spectroscopy information of the reservoir fluid can be obtained using the present invention, as can the velocity profile of the flowing fluid inside the sample tube.

While protons are normally the spins of interest in NMR experiments, other spins may be used. For example, certain isotopes of carbon, phosphorus, or fluorine have spins that can produce an NMR response. The present invention can be adapted to perform NMR experiments on any sample containing spins capable of producing an NMR response.

Electron spin resonance (ESR, also known as electron paramagnetic resonance, EPR) occurs, for example, when an atom has an unpaired electron. It may also occur for paramagnetic compounds such as oxygen ($O_2$) and free radicals such as a chlorine atom. Certain metals, such as vanadium, also combine with organic compounds such that unpaired electrons stably exist. Magnetic resonance experiments can be performed on samples exhibiting ESR, and the present invention allows such experiments to be performed downhole.

Multiple micro NMR analyzers can be used simultaneously or sequentially. This allows investigation of different spins or compositions and yields multiple data points. This is in contrast to existing downhole NMR tools for which it is impractical to use one NMR tool in proximity to other NMR tools.

The present invention can be fabricated using micro fabrication techniques with the entire apparatus constructed on a chip 13. Alternatively, a portion of the apparatus can be made on chip 13. This is particularly so for the sample tube 16 and micro RF coils 14. The magnets 12 may or may not be fabricated directly on the chip 13.

While the invention has been described with respect to a limited number of embodiments, those skilled in the art, having benefit of this disclosure, will appreciate that other embodiments can be envisioned that do not depart from the scope of the invention as disclosed herein. Accordingly, the scope of the invention shall be limited only by the attached claims.

What is claimed is:

1. A downhole micro MR analyzer comprising:
   a micro sample tube connected to a downhole wellbore sampling tube, the micro sample tube comprises
      a substrate having a passageway formed therein for transporting a reservoir fluid;
   a micro RF coil in close proximity to the micro sample tube wherein at least a portion of the coil is etched directly onto the micro sample tube; and
   one or more magnets micro-fabricated by constructing at least one of the magnets directly on the substrate comprising the micro sample tube, the one or more magnets generating a magnetic field into the micro sample tube.

2. The downhole micro MR analyzer of claim 1, wherein the micro MR analyzer is a micro NMR analyzer or a micro ESR analyzer.

3. The downhole micro MR analyzer of claim 1, wherein the micro RF is a Helmholts coil having two coils arranged with planes parallel and separated a distance substantially similar to a diameter of one of the coils.

4. The downhole micro MR analyzer of claim 1, wherein the micro RF coil has a spiral portion etched on a printed circuit board and attached to the micro sample tube.

5. The downhole micro MR analyzer of claim 1, further comprising a sample delivery channel fluidly connected to the micro sample tube, the sample delivery channel including means for generating a static magnetic field within the sample delivery channel to pre-polarize at least a portion of the reservoir fluid nor to entering the micro sample tube.

6. The downhole micro MR analyzer of claim 1, further comprising a sample delivery channel in fluid communication with the micro sample tube.

7. The downhole micro MR analyzer of claim 1, wherein the one or more magnets are permanent magnets.

8. The downhole micro MR analyzer of claim 1, wherein the micro RF coil comprises a Helmholtz coil having two coils arranged with planes parallel and separated a distance substantially similar to a diameter of the two coils.

9. The downhole micro MR analyzer of claim 1, wherein the micro RF coil is a spiral, substantially planar coil.

10. The downhole micro MR analyzer of claim 1, further comprising one or more gradient coils.

11. The downhole micro MR analyzer of claim 1, further comprising permeable magnetic material.

12. The downhole micro MR analyzer of claim 1, wherein all of the analyzer is constructed on a chip using micro fabrication techniques.

13. A downhole micro MR analyzer system comprising:
a micro RF coil;
a micro-strip line with a first conductive trace on a dielectric material mounted onto a second conductive trace;
a slit through the micro strip line forming a micro sample tube; and
a magnet disposed about the micro sample tube, with the micro sample tube connected to a downhole wellbore sampling tool in order to transport reservoir fluid through the analyzer system.

14. The system of claim 13 wherein two of the micro analyzers are used sequentially or simultaneously to determine different spins or compositions.

15. A method to perform a MR experiment in a wellbore, comprising:
sampling a reservoir fluid with a downhole wellbore sampling device;
transporting the reservoir fluid to a downhole micro MR analyzer in the wellbore, the downhole micro MR analyzer comprising:
a micro sample tube;
a micro RF coil in close proximity to the micro sample tube, the micro RF coil etched on a printed circuit board and attached to the micro sample tube; and
one or more magnets disposed about the micro sample tube in order to generate a magnetic field within the micro sample tube;
obtaining a portion of the reservoir fluid in the micro sample tube;
polarizing the portion of the reservoir fluid with the one or more magnets;
irradiating the portion of the reservoir fluid sample with RF signal from the micro RF coil; and
measuring the MR response from the portion of the reservoir fluid in order to ascertain properties of the wellbore, formation about the wellbore or the fluid sample.

16. The method of claim 15, further comprising energizing one or more gradient coils.

17. The method of claim 15, further comprising pre-polarizing the fluid sample.

18. The method of claim 15, wherein the measuring the MR response comprises measuring spin-lattice relaxation time, spin-spin relaxation time, diffusion, molecular composition, hydrogen index, water saturation, chemical shift, spectroscopy, or any combination of those measurements.

19. The method of claim 15, wherein the measuring the MR response comprises measuring the NMR response from proton spins or spins other than proton spins.

* * * * *